US009872621B2

(12) United States Patent
Falconer et al.

(10) Patent No.: US 9,872,621 B2
(45) Date of Patent: Jan. 23, 2018

(54) MULTISPECTRAL MEASUREMENT FOR IMPROVED BIOLOGICAL SIGNAL ACQUISITION

(71) Applicant: Intel Corporation, Santa Clara, CA (US)

(72) Inventors: Maynard C. Falconer, Portland, OR (US); Willem M. Beltman, West Linn, OR (US)

(73) Assignee: Intel Corporation, Santa Clara, CA (US)

( * ) Notice: Subject to any disclaimer, the term of this patent is extended or adjusted under 35 U.S.C. 154(b) by 426 days.

(21) Appl. No.: 14/572,938

(22) Filed: Dec. 17, 2014

(65) Prior Publication Data
US 2016/0174843 A1 Jun. 23, 2016

(51) Int. Cl.
*A61B 5/1455* (2006.01)
*A61B 5/00* (2006.01)

(52) U.S. Cl.
CPC .......... *A61B 5/0042* (2013.01); *A61B 5/0075* (2013.01); *A61B 5/0086* (2013.01);
(Continued)

(58) Field of Classification Search
CPC ... A61B 5/0002; A61B 5/0059; A61B 5/1455; A61B 5/14552; A61B 5/14553; A61B 5/14532; A61B 5/0042; A61B 5/0075; A61B 5/0086; A61B 5/7221; A61B 5/7278; A61B 5/14551
See application file for complete search history.

(56) References Cited

U.S. PATENT DOCUMENTS

| 5,827,182 | A | 10/1998 | Raley | |
| 6,587,701 | B1 * | 7/2003 | Stranc | A61B 5/14551 600/310 |
| 2001/0056237 | A1 | 12/2001 | Cane | |
| 2005/0080323 | A1 * | 4/2005 | Kato | A61B 5/14553 600/323 |

(Continued)

FOREIGN PATENT DOCUMENTS

| TW | M447757 | 3/2013 |
| TW | 201406348 | 2/2014 |
| WO | 2013163443 | 10/2013 |

OTHER PUBLICATIONS

Taiwan Intellectual Property Office, Office Action dated Nov. 17, 2016, in Taiwanese Patent Application No. 104137353.
(Continued)

*Primary Examiner* — Eric Winakur
*Assistant Examiner* — Chu Chuan (JJ) Liu
(74) *Attorney, Agent, or Firm* — Trop, Pruner & Hu, P.C.

(57) ABSTRACT

An embodiment includes a functional near infrared (fNIR) system comprising: first, second, and third light emitting diodes (LED) and a photo detector; and at least one storage medium having instructions stored thereon for causing the system to: (a) emit photo energy at first, second, and third wavelengths from the first, second, and third LEDs during first and second time periods, (b) determine first, second, and third optical density changes and changes in first and second chromophore concentrations based on the emitted photo energy; and (c) determine and fit first, second, and third absorption values to a first absorption spectra curve based on the determined changes in first and second chromophore concentrations. Other embodiments are described herein.

24 Claims, 4 Drawing Sheets

(52) U.S. Cl.
CPC ...... *A61B 5/14551* (2013.01); *A61B 5/14552* (2013.01); *A61B 5/7221* (2013.01); *A61B 5/7278* (2013.01); *A61B 2560/0475* (2013.01); *A61B 2562/0238* (2013.01); *A61B 2562/046* (2013.01); *A61B 2576/026* (2013.01)

(56) References Cited

U.S. PATENT DOCUMENTS

| | | |
|---|---|---|
| 2005/0256384 A1 | 11/2005 | Walker |
| 2008/0221426 A1 | 9/2008 | Baker et al. |

OTHER PUBLICATIONS

International Searching Authority, "Notification of Transmittal of the International Search Report and the Written Opinion of the International Searching Authority," dated Feb. 25, 2016 in International application No. PCT/US2015/060986.

Artinis Medical Systems, "Applications of NIRS," http://www.artinis.com/product/oximetry_applications, The Netherlands, pp. 1-8, 2014.

BIOPAC Systems, Inc., "fNIR Optical Brain Imaging System: Product Sheet," BIOPAC Hardware, pp. 1-5, Sep. 25, 2014.

Wikipedia, "Functional near-infrared spectroscopy," http://en.wikipedia.org/wiki/Functional_near-infrared_spectroscopy, pp. 1-6, Nov. 2014.

Artinis Medical Systems, "Introduction," http://www.artinis.com/product/introduction, The Netherlands, pp. 1-8, 2014.

Wikipedia, "Molar absorptiity," http://en.wikipedia.org/wiki/Molar_absorptivity, pp. 1-2, Dec. 2014.

Boas, David et al., "Near infrared imaging," http://www.scholarpedia.org/article/Near_infrared_imaging, pp. 1-7, 2009.

* cited by examiner

MULTISPECTRAL MEASUREMENT FOR IMPROVED BIOLOGICAL SIGNAL ACQUISITION

BACKGROUND

Functional near infra-red spectroscopy (fNIR) is a non-invasive imaging method involving the quantification of chromophore concentration resolved from the measurement of near infrared (NIR) light attenuation, temporal or phasic changes. fNIR may be used to detect brain activity (i.e., neural load) by measuring blood oxygenation levels in the brain as an indicator of brain activity in a local area. Specifically, fNIR may use infrared light emitting diodes (LEDs) at two different wavelengths to detect the blood oxygenation levels needed to determine brain activity. The infrared (IR) wavelengths are chosen to be within the IR "window" of tissue, skin, and bone (e.g., 700 nm-900 nm) and to correspond to the IR absorption by hemoglobin and oxygenated hemoglobin. A change in the concentration levels of hemoglobin and oxygenated hemoglobin may be determined using the modified Beer-Lambert law: $OD=-\log (I/I_o)=\epsilon[X]d \times DPF+G$ where OD is the optical density of the sample as determined from the negative log ratio of the detected intensity of light I with respect to the incident intensity of light $I_o$. The OD is related to the absorption coefficient of the tissue $\epsilon$, [X] is the chromophore concentration, and d is the net distance traveled by the light from the source to the detector scaled by the differential pathlength factor DPF, plus a geometry factor G.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner.

Figure 1:
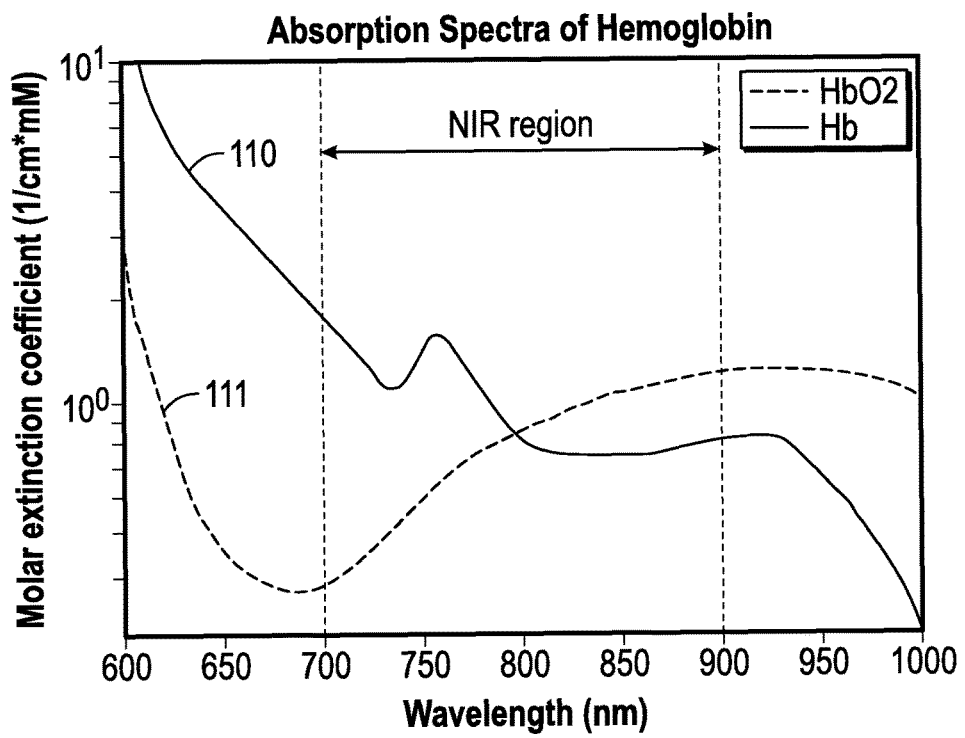
FIG. 1 includes absorption spectra curves for hemoglobin and oxygenated hemoglobin.

As previously described, conventional fNIR systems consist of an array of IR sources and IR detectors, where the IR sources are at two wavelengths. The fNIR systems use the two wavelengths to determine the relative quantities (e.g., concentrations) of hemoglobin to oxygenated hemoglobin, which may provide a measure of brain activity in a local region. This is done by using known values, such as the intrinsic molar extinction coefficient of the tissue $\epsilon$ for hemoglobin to oxygenated hemoglobin as shown in FIG. 1. Accurately determining relative quantities of hemoglobin to oxygenated hemoglobin can be quite problematic because the received signals (e.g., $I/I_o$) are very small and have large noise components. The conventional mechanism for improving the signal to noise ratio (SNR) for the captured data includes time averaging over multiple samples, which results in longer measurement times.

However, an embodiment provides much improved signal quality and data capture, which leads to more accurate assessments (e.g., cognitive load assessment) that are obtained more quickly than is possible with conventional systems. An embodiment combines known values (e.g., wavelength versus absorption characteristics shown in FIG. 1) with measurements at multiple (e.g., three or more) wavelengths to obtain a superior SNR result than can be achieved with a smaller number of total samples. This leads to faster assessments. Additionally, an embodiment provides that information regarding the proper target (i.e., hemoglobin concentration versus oxygenated hemoglobin concentration) is extracted from the fit of data points (absorption values) to the expected wavelength versus absorption profile. For example, the lack of fit (or improper fit) of the data to the anticipated shape of either the hemoglobin or oxygenated hemoglobin absorption curves indicates the wrong chromophore may have been detected (e.g., something other than hemoglobin or oxygenated hemoglobin or even confusion between hemoglobin and oxygenated hemoglobin). An embodiment provides a low confidence level output (e.g., visual or auditory) when the absorption value does not have a strong fit to the expected wavelength versus absorption profile, which may indicate equipment malfunction or that equipment is not properly fitted to the subject (e.g., not properly attached to patient's skull). Thus, various embodiments improve signal acquisition for fNIR systems, deliver superior quality of data, and reduce data acquisition time allowing for real time (or near real time) measurement of data. For example, an embodiment reduces the number of $I/I_o$ measurement averages needed to provide reliable chromophore concentration information; therefore reducing the data acquisition and processing time and providing faster data acquisition and feedback to the user.

FIG. 1 includes absorption spectra curves for hemoglobin (110) and oxygenated hemoglobin (111). The shape of the absorption (Y axis) versus wavelength (X axis) curves for both hemoglobin and oxygenated hemoglobin are fixed quantities. As the amount (e.g., concentration) of hemoglobin and oxygenated hemoglobin change, the absorption curves move up and down relative to each other (but the shapes of the curves remain the same).

Figure 2:
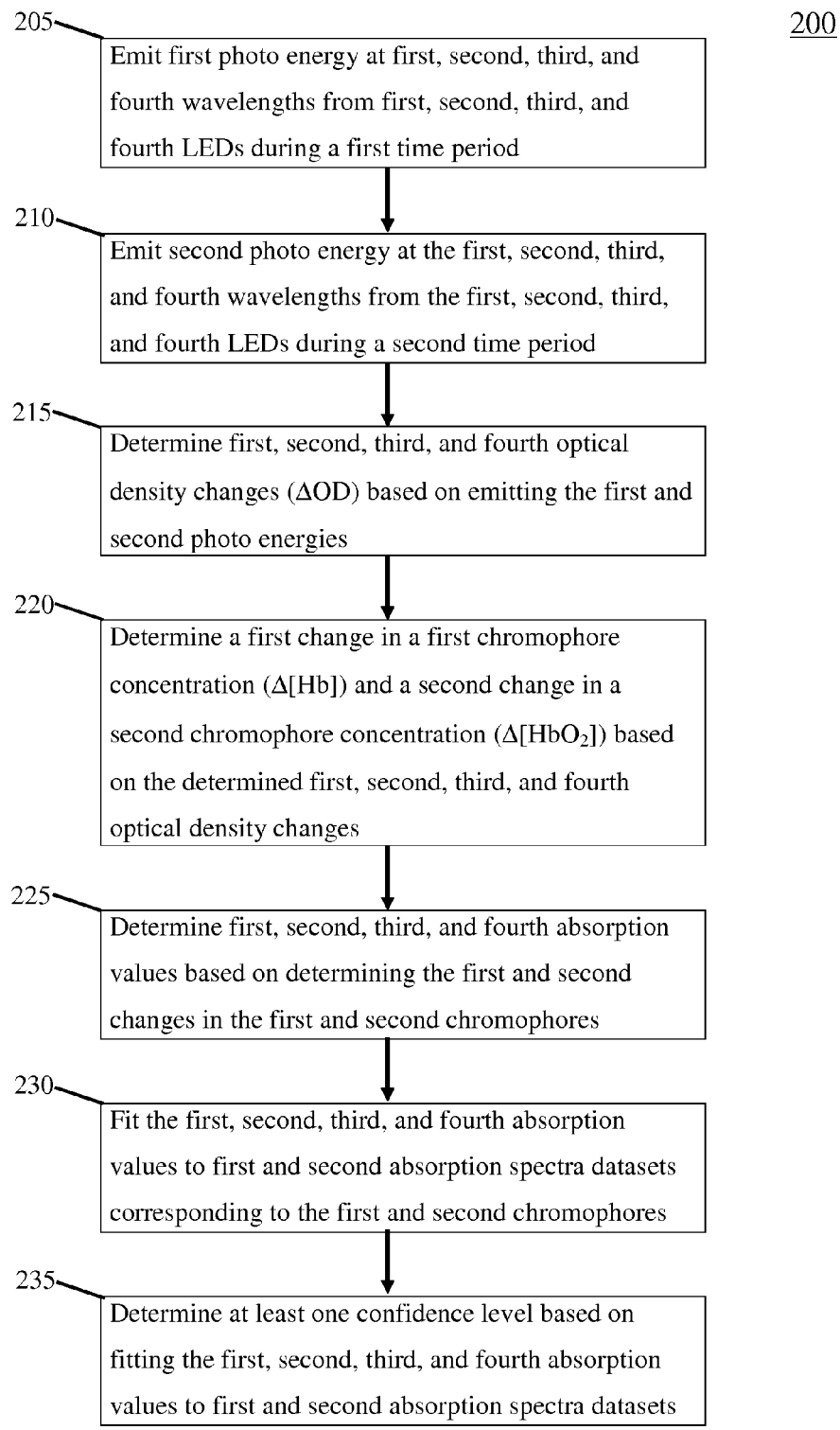
FIG. 2 includes a process for fitting absorption values to absorption spectra curves for hemoglobin and oxygenated hemoglobin in an embodiment of the invention.

FIG. 2 includes a process 200 for fitting absorption values to absorption spectra curves for hemoglobin and oxygenated hemoglobin in an embodiment of the invention.

Figure 3:
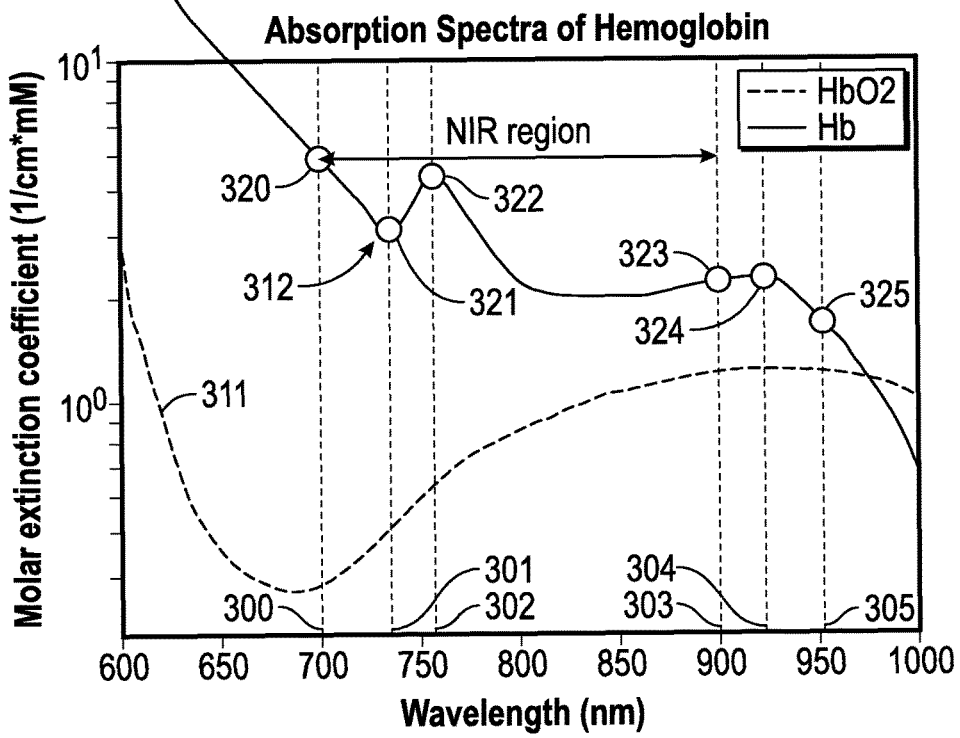
FIG. 3 includes curve fitting absorption values to absorption spectra curves for hemoglobin and oxygenated hemoglobin in an embodiment of the invention when oxygenated hemoglobin concentration is low and hemoglobin concentration is high.

In block 205 a fNIR system emits first photo energy at first, second, third, and fourth wavelengths from first, second, third, and fourth LEDs, or other infrared sources, during a first time period. In an embodiment the first, second, third, and fourth wavelengths are unequal to each other. In an embodiment the first and second wavelengths are between 650 nm and 800 nm and the third and fourth wavelengths are between 800 nm and 950 nm. For example, FIG. 3 includes curve fitting absorption values to absorption spectra curves for hemoglobin and oxygenated hemoglobin in an embodiment of the invention when oxygenated hemoglobin concentration is low and hemoglobin concentration is high. Specifically, in FIG. 3 first and second wavelengths (301, 302) are between 650 nm and 800 nm and the third and fourth wavelengths (303, 304) are between 800 nm and 950 nm. Embodiments may also utilize other wavelengths to increase accuracy, such as wavelengths 300, 305, which may or may not be within 650 nm and 950 nm considering embodiments are not strictly related to fNIR and hemoglobin and oxygenated hemoglobin detection. In FIG. 3, first and second absorption spectra datasets correspond to first and second absorption spectra curves 310 (hemoglobin), 311 (oxygenated hemoglobin).

As mentioned above, embodiments use more wavelength measurements than conventions systems. However, the selection of the wavelengths also differs from conventional systems. For example, in FIG. 3 the wavelength 301 corresponds to a location at or less than an inflection point 312 for the absorption spectra curve 310 and the wavelength 302 corresponds to an additional location greater than the inflection point 312. An inflection point, such as point 312, is a point of a curve at which a change in the direction of curvature occurs. In addition, wavelength 300 corresponds to an additional location less than the inflection point 312. By bracketing (choosing wavelengths on both sides of inflection point) or at least targeting the wavelength corresponding to the known inflection point 312 an embodiment is better able to distinguish between chromophore concentrations (e.g., [Hb], [HbO$_2$]), as will be made more evident in the discussion below that addresses FIG. 5.

While not shown in block 205, not only is photo energy emitted but $I/I_o$ (or more specifically, $I_o$) is sensed.

In block 210 the system emits second photo energy at the first, second, third, and fourth wavelengths from the first, second, third, and fourth LEDs during a second time period. For example, the time period referenced in block 205 may relate to a "rest" state for the subject and the time period in block 210 may related to a "test" state for the subject. Furthermore, emitting second photo energy at the first, second, third, and fourth wavelengths from the first, second, third, and fourth LEDs during a second time period does not necessarily mean the energy is emitted simultaneously from the LEDs (but in some embodiments the emission is indeed simultaneous). In some embodiments the photo emission may be serial in nature with emissions quickly following one another without overlapping one another. The same is true for the emission of photo energy in block 205.

In block 215 the system determines first, second, third, and fourth optical density changes ($\Delta$OD) based on emitting the first and second photo energies. For example, $\Delta OD_{\lambda 1} = (\epsilon Hb_{\lambda 1}[\Delta Hb] + \epsilon HbO_{2\lambda 1}[\Delta HbO_2]) \times d \times DPF$; $\Delta OD_{\lambda 2} = (\epsilon Hb_{\lambda 2}[\Delta Hb] + \epsilon HbO_{2\lambda 2}[\Delta HbO_2]) \times d \times DPF$; $\Delta OD_{\lambda 3} = (\epsilon Hb_{\lambda 3}[\Delta Hb] + \epsilon HbO_{2\lambda 3}[\Delta HbO_2]) \times d \times DPF$; $\Delta OD_{\lambda 4} = (\epsilon Hb_{\lambda 4}[\Delta Hb] + \epsilon HbO_{2\lambda 4}[\Delta HbO_2]) \times d \times DPF$; ... $\Delta OD_{\lambda n} = (\epsilon Hb_{\lambda n}[\Delta Hb] + \epsilon HbO_{2\lambda n}[\Delta HbO_2]) \times d \times DPF$ (where n is the total number of wavelengths sensed). Thus, determining four optical density changes does not preclude determining additional changes if $n > 4$.

In block 220 the system determines a first change in a first chromophore concentration ($\Delta$[Hb]) and a second change in a second chromophore concentration ($\Delta$[HbO$_2$]) based on the determined first, second, third, and fourth OD changes. For example, an embodiment solves for the concentration changes as follows:

$$\begin{bmatrix} \Delta OD_{\lambda 1} \\ \Delta OD_{\lambda 2} \\ * \\ \Delta OD_{\lambda n} \end{bmatrix} = \begin{bmatrix} \varepsilon_{\lambda 1}^{HB}.d.DPF & \varepsilon_{\lambda 1}^{HBO_2}.d.DPF \\ \varepsilon_{\lambda 2}^{HB}.d.DPF & \varepsilon_{\lambda 2}^{HBO_2}.d.DPF \\ * & *** \\ \varepsilon_{\lambda n}^{HB}.d.DPF & \varepsilon_{\lambda n}^{HBO_2}.d.DPF \end{bmatrix} \begin{bmatrix} \Delta c^{HB} \\ \Delta c^{HBO_2} \end{bmatrix} \quad \text{(Matrix 1)}$$

As seen in Matrix 1, an embodiment utilizes an overdetermined system by using three or more wavelengths to determine the one or two chromophore concentrations. A system of linear equations is considered overdetermined if there are more equations than unknowns. The terminology can be described in terms of the concept of constraint counting. Each unknown can be seen as an available degree of freedom. Each equation introduced into the system can be viewed as a constraint that restricts one degree of freedom. Thus, in an embodiment the fNIR system determines, via an overdetermined system, changes in the chromophore concentrations based on the determined OD changes.

In block 225 the system determines first, second, third, and fourth absorption values based on determining the first and second changes in the first and second chromophores. In block 230 the system fits the first, second, third, and fourth absorption values to first and second absorption spectra datasets corresponding to the first and second chromophores. As seen in FIG. 3, absorption values 320, 321, 322, 323, 324, 325 are determined. FIG. 3 depicts a unique situation where oxygenated hemoglobin concentration is low and hemoglobin concentration is high.

Regarding curve fitting, an embodiment uses mean square error (MSE) for fitting the absorption values 320, 321, 322, 323, 324, 325 to curves 310, 311 (which are based on absorption spectra datasets for the two chromophores). In statistics, the MSE of an estimator measures the average of the squares of the "errors", that is, the difference between the estimator and what is estimated.

Curve fitting is the process of constructing a curve, or mathematical function, which has the best fit to a series of data points, possibly subject to constraints. Curve fitting can involve either interpolation, where an exact fit to the data is required, or smoothing, in which a "smooth" function is constructed that approximately fits the data. A related topic is regression analysis, which focuses more on questions of statistical inference such as how much uncertainty (e.g., a "confidence level") is present in a curve that is fit to data observed with random errors. Fitted curves can be used as an aid for data visualization, to infer values of a function where no data are available, and to summarize the relationships among two or more variables.

The method of least squares is an approach to the approximate solution of overdetermined systems. "Least squares" means that the overall solution minimizes the sum of the squares of the errors made in the results of every single equation. Least-squares may be used in data fitting/curve fitting. The best fit in the least-squares sense minimizes the sum of squared residuals, a residual being the difference between an observed value and the fitted value provided by a model. Of course, other curve fitting techniques are used in other embodiments.

Returning to FIG. 3, an embodiment uses MSE and Matrix 1 for fitting the absorption values to curves 310, 311. However, the embodiment also uses MSE for fitting the absorption values to just curve 310, whereby Matrix 1 is used to solve only for [ΔHb] and not [ΔHbO$_2$]. In such case, the modified Matrix 1 has a MSE the same as that for unmodified Matrix 1 (solving for both [ΔHb] and [ΔHbO$_2$]) since oxygenated hemoglobin is best fit with zero when all 6 data points 320, 321, 322, 323, 324, 325 are used. In such a case the embodiment has clearly distinguished the data between the two chromophores showing the dominance of hemoglobin over oxygenated hemoglobin.

In block 235 the system determines at least one confidence level based on fitting the first, second, third, and fourth absorption values to first and second absorption spectra datasets. Based on the low MSE associated with the modified form of Matrix 1 (solving only for [ΔHb]) (i.e., strong fit to curve 310) a high confidence level is found regarding the [ΔHb] and [ΔHbO$_2$] and the user can be more assured the data is accurate and the equipment is functioning properly.

Figure 4:
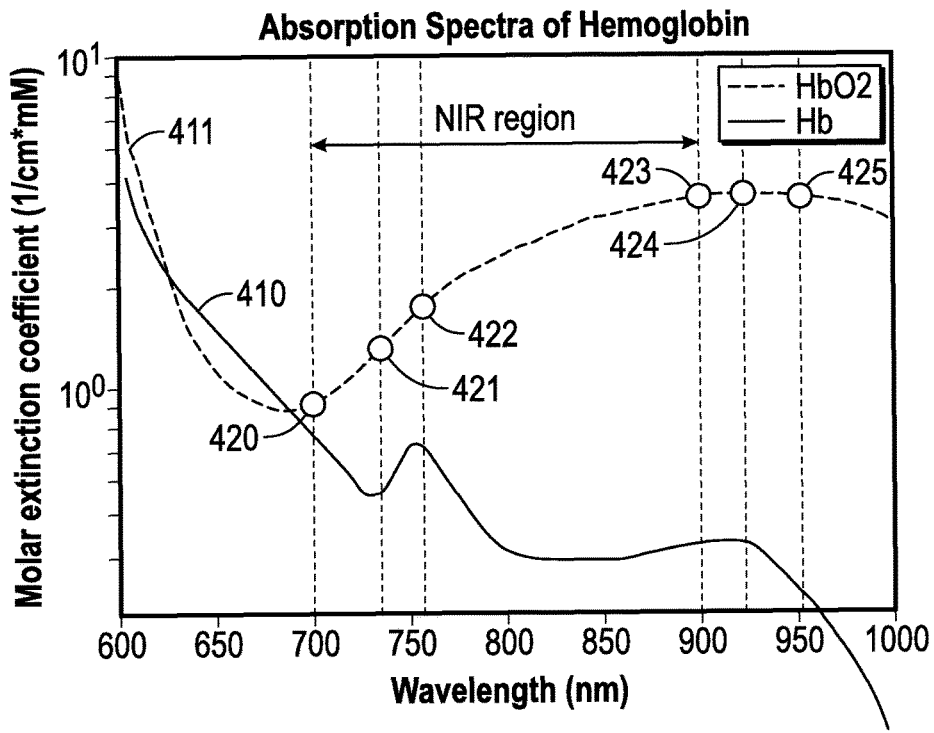
FIG. 4 includes curve fitting absorption values to absorption spectra curves for hemoglobin and oxygenated hemoglobin in an embodiment of the invention when oxygenated hemoglobin concentration is high and hemoglobin concentration is low.

Returning to block 225 (but addressing the data of FIG. 4 instead of FIG. 3) the system determines first, second, third, and fourth absorption values based on determining the first and second changes in the first and second chromophores. In block 230 the system fits the first, second, third, and fourth absorption values to first and second absorption spectra datasets corresponding to the first and second chromophores. As seen in FIG. 4, absorption values 420, 421, 422, 423, 424, 425 are determined. FIG. 4 depicts a unique situation where the oxygenated hemoglobin concentration is high and the hemoglobin concentration is low.

Regarding curve fitting, an embodiment uses mean square error for fitting the absorption values to curves 410, 411 (which are based on absorption spectra datasets for the two chromophores). For FIG. 4 an embodiment uses MSE and Matrix 1 for fitting the absorption values to curves 410, 411. However, the embodiment also uses MSE for fitting the absorption values to just curve 411, whereby Matrix 1 is used to solve only for [ΔHbO$_2$] and not [ΔHb]. In such a case, the modified Matrix 1 has a MSE the same as that for unmodified Matrix 1 (solving for both [ΔHb] and [ΔHbO$_2$]) since hemoglobin is best fit with zero when all 6 data points 420, 421, 422, 423, 424, 425 are used. In such a case the embodiment has clearly distinguished the data between the two chromophores showing the dominance of oxygenated hemoglobin over hemoglobin.

In block 235 the system determines at least one confidence level based on fitting the first, second, third, and fourth absorption values (e.g., any four or more of data points 420, 421, 422, 423, 424, 425) to first and second absorption spectra datasets. Based on the low MSE associated with the modified form of Matrix 1 (solving only for [ΔHbO$_2$]) (i.e., strong fit to curve 411) a high confidence level is found regarding the [ΔHb] and [ΔHbO$_2$] and the user can be more assured the data is accurate and the equipment is functioning properly.

Figure 5:
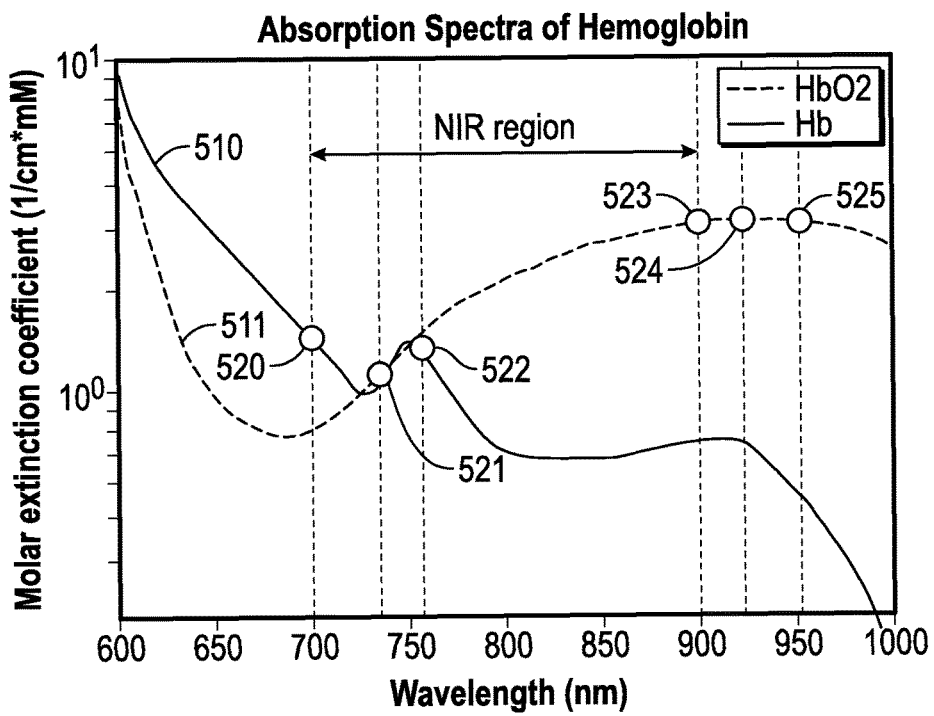
FIG. 5 includes curve fitting absorption values to absorption spectra curves for hemoglobin and oxygenated hemoglobin in an embodiment of the invention when oxygenated hemoglobin concentration and hemoglobin concentration are similar to each other.

Returning to block 225 (but addressing the data of FIG. 5 instead of FIG. 3 or 4) the system determines first, second, third, and fourth absorption values based on determining the first and second changes in the first and second chromophores. In block 230 the system fits the first, second, third, and fourth absorption values to first and second absorption spectra datasets corresponding to the first and second chromophores. As seen in FIG. 5, absorption values 520, 521, 522, 523, 524, 525 are determined. FIG. 5 depicts a unique situation where oxygenated hemoglobin concentration and hemoglobin concentration are similar to each other. For example, curves 510, 511 are very similar between the 700 nm to 760 nm range.

Regarding curve fitting, an embodiment uses MSE for fitting the absorption values to curves 510, 511 (which are based on absorption spectra datasets for the two chromophores). For FIG. 5 an embodiment uses MSE and Matrix 1 for fitting the absorption values to curves 510, 511. However, the embodiment also uses MSE for fitting the absorption values to just curve 510 for the 700 nm to 760 nm wavelength range, whereby Matrix 1 is used to solve only for [ΔHb] and not [ΔHbO$_2$]. In such case, MSE is lowest for deoxygenated hemoglobin [ΔHb] when fit with the three points 520, 521, 522 between 700-760 nm. In this scenario the conventional approach would not be able disambiguate lines 510, 511 from the 700-760 nm points (since the conventional method would only have one data point in this region). But an embodiment can distinguish between lines 510, 511, even in difficult conditions such as those between 700-760 nm in FIG. 5 by examining the MSE of those three data points 520, 521, 522. A similar analysis could be performed for the 900 nm-960 nm range for data points 523, 524, 525 showing a best fit to curve 511 based on MSE.

In block 235 the system determines at least one confidence level based on fitting the first, second, third, and fourth absorption values to first and second absorption spectra datasets. Based on the low MSE associated with the modified form of Matrix 1 (solving only for [ΔHb]) (i.e., strong fit to curve 510) a high confidence level is found regarding the [ΔHb] and [ΔHbO$_2$] and the user can be more assured the data is accurate and the equipment is functioning properly.

FIGS. 2-5 and the related discussion are illustrative examples only and do not limit embodiments to a specific number of wavelengths sampled, nor the selection of wavelengths for the measurements. Embodiments may be changed to use wavelengths that provide the best prediction of characteristic shapes, whether those are for hemoglobin/oxygenated hemoglobin chromophores or other chromophores. There are many available techniques for determination of the absorption shape level including, for example, minimizing the RMS error between the measured points and the expected shape. The shape (e.g., curves 510, 511) can be represented by a look up table, polynomial equation, or other mathematical function.

Embodiments may be used in medical devices (e.g., assess cognitive load to research brain damage), consumer electronics (e.g., assess cognitive load to determine fitness to operate a motorized vehicle after a long sleep deprivation period), and health/fitness devices concerning brain computer interfaces (BCI), either as a standalone modality or in combination with existing modalities.

Hardware for an embodiment may include a plurality of LEDs, or other infrared sources, and one or more sensors. The LEDs may provide simultaneous or non-simultaneous emission of more than two IR wavelengths in the 700-900 nm range. In an embodiment the LEDs are all generally equidistant from the photo detector used to sense their output FIG. 6 includes a system for implementing processes in an embodiment of the invention. fNIR systems discussed herein may utilize a system such as the system of FIG. 6, discussed below. In fact, embodiments may be used in many different types of systems. For example, in one embodiment a communication device can be arranged to perform the various methods and techniques described herein. Of course, the scope of the present invention is not limited to a communication device, and instead other embodiments can be directed to other types of apparatus for processing instructions.

Program instructions may be used to cause a general-purpose or special-purpose processing system that is programmed with the instructions to perform the operations described herein. Alternatively, the operations may be performed by specific hardware components that contain hard-wired logic for performing the operations, or by any combination of programmed computer components and custom hardware components. The methods described herein may be provided as (a) a computer program product that may include one or more machine readable media having stored thereon instructions that may be used to program a processing system or other electronic device to perform the methods or (b) at least one storage medium having instructions stored thereon for causing a system to perform the methods. The term "machine readable medium" or "storage medium" used herein shall include any medium that is capable of storing or encoding a sequence of instructions (transitory media, including signals, or non-transitory media) for execution by the machine and that cause the machine to perform any one of the methods described herein. The term "machine readable medium" or "storage medium" shall accordingly include, but not be limited to, memories such as solid-state memories, optical and magnetic disks, read-only memory (ROM), programmable ROM (PROM), erasable PROM (EPROM), electrically EPROM (EEPROM), a disk drive, a floppy disk, a compact disk ROM (CD-ROM), a digital versatile disk (DVD), flash memory, a magneto-optical disk, as well as more exotic mediums such as machine-accessible biological state preserving or signal preserving storage. A medium may include any mechanism for storing, transmitting, or receiving information in a form readable by a machine, and the medium may include a medium through which the program code may pass, such as antennas, optical fibers, communications interfaces, etc. Program code may be transmitted in the form of packets, serial data, parallel data, etc., and may be used in a compressed or encrypted format. Furthermore, it is common in the art to speak of software, in one form or another (e.g., program, procedure, process, application, module, logic, and so on) as taking an action or causing a result. Such expressions are merely a shorthand way of stating that the execution of the software by a processing system causes the processor to perform an action or produce a result.

Figure 6:
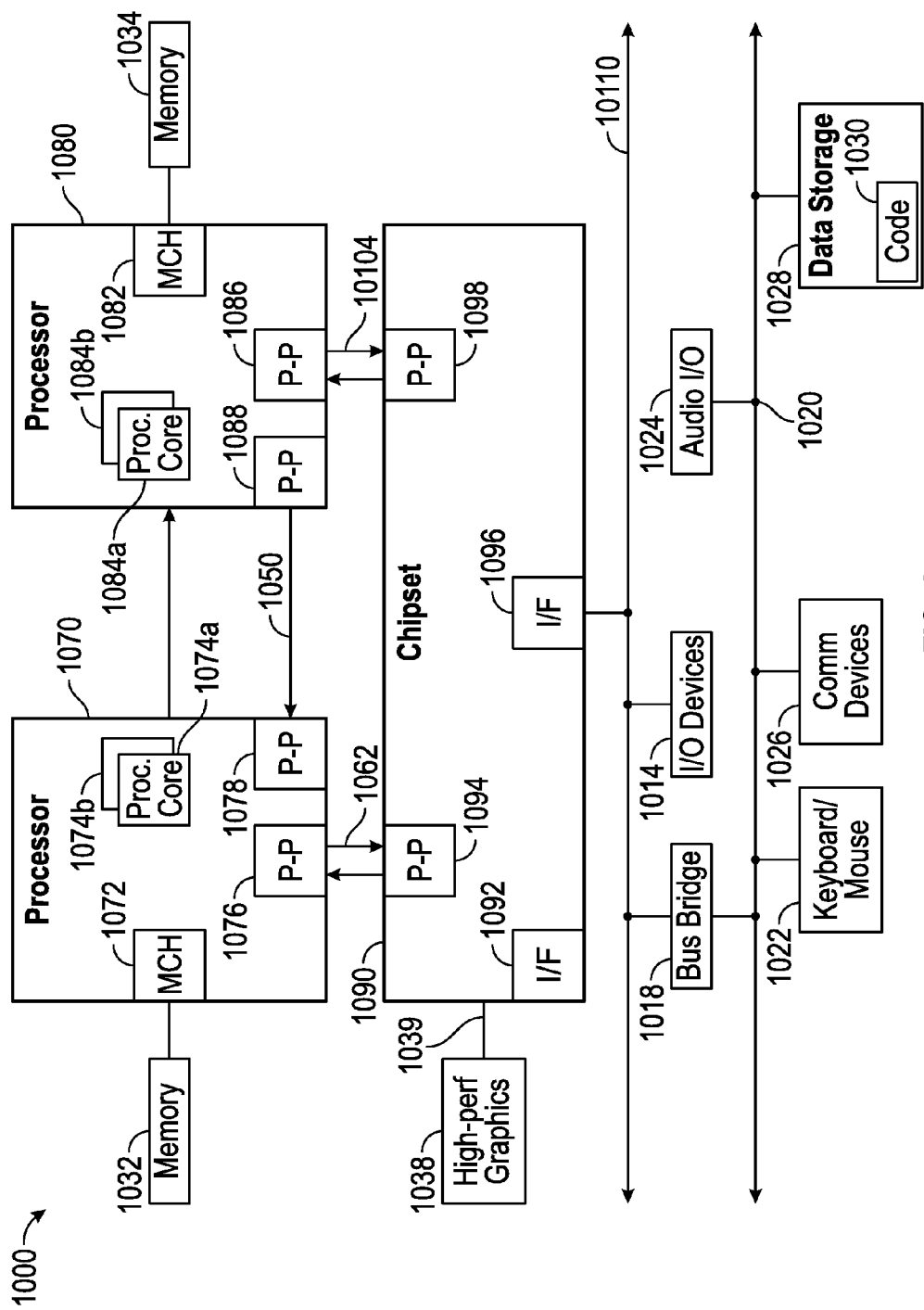
FIG. 6 includes a system for implementing processes in an embodiment of the invention.

Referring now to FIG. 6, shown is a block diagram of a system embodiment 1000 in accordance with an embodiment of the present invention. System 1000 may be included in, for example, a mobile computing node such as a cellular phone, smartphone, tablet, Ultrabook®, notebook, laptop, personal digital assistant, wearable internet connected devices (e.g., wrist bands, head bands, spectacles, athletic helmets, military helmets, baseball caps, hats) and mobile processor based platform. Embodiments may include headbands that include the LEDs and sensor or sensors with wireless capacity to communicate with a cloud based system that in turn directs some or all of photo emission and detection and/or chromophore concentration determination.

Shown is a multiprocessor system 1000 that includes a first processing element 1070 and a second processing element 1080. While two processing elements 1070 and 1080 are shown, it is to be understood that an embodiment of system 1000 may also include only one such processing element. System 1000 is illustrated as a point-to-point interconnect system, wherein the first processing element 1070 and second processing element 1080 are coupled via a point-to-point interconnect 1050. It should be understood that any or all of the interconnects illustrated may be implemented as a multi-drop bus rather than point-to-point interconnect. As shown, each of processing elements 1070 and 1080 may be multicore processors, including first and second processor cores (i.e., processor cores 1074a and 1074b and processor cores 1084a and 1084b). Such cores 1074, 1074b, 1084a, 1084b may be configured to execute instruction code in a manner similar to methods discussed herein.

Each processing element 1070, 1080 may include at least one shared cache. The shared cache may store data (e.g., instructions) that are utilized by one or more components of the processor, such as the cores 1074a, 1074b and 1084a, 1084b, respectively. For example, the shared cache may locally cache data stored in a memory 1032, 1034 for faster access by components of the processor. In one or more embodiments, the shared cache may include one or more mid-level caches, such as level 2 (L2), level 3 (L3), level 4 (L4), or other levels of cache, a last level cache (LLC), and/or combinations thereof.

While shown with only two processing elements 1070, 1080, it is to be understood that the scope of the present invention is not so limited. In other embodiments, one or more additional processing elements may be present in a given processor. Alternatively, one or more of processing elements 1070, 1080 may be an element other than a processor, such as an accelerator or a field programmable gate array. For example, additional processing element(s) may include additional processors(s) that are the same as a first processor 1070, additional processor(s) that are heterogeneous or asymmetric to first processor 1070, accelerators (such as, e.g., graphics accelerators or digital signal processing (DSP) units), field programmable gate arrays, or any other processing element. There can be a variety of differences between the processing elements 1070, 1080 in terms of a spectrum of metrics of merit including architectural, microarchitectural, thermal, power consumption characteristics, and the like. These differences may effectively manifest themselves as asymmetry and heterogeneity amongst the processing elements 1070, 1080. For at least one embodiment, the various processing elements 1070, 1080 may reside in the same die package.

First processing element 1070 may further include memory controller logic (MC) 1072 and point-to-point (P-P) interfaces 1076 and 1078. Similarly, second processing element 1080 may include a MC 1082 and P-P interfaces 1086 and 1088. MC's 1072 and 1082 couple the processors to respective memories, namely a memory 1032 and a memory 1034, which may be portions of main memory locally attached to the respective processors. While MC logic 1072 and 1082 is illustrated as integrated into the processing elements 1070, 1080, for alternative embodiments the MC logic may be discreet logic outside the processing elements 1070, 1080 rather than integrated therein.

First processing element 1070 and second processing element 1080 may be coupled to an I/O subsystem 1090 via P-P interfaces 1076, 1086 via P-P interconnects 1062, 10104, respectively. As shown, I/O subsystem 1090 includes P-P interfaces 1094 and 1098. Furthermore, I/O subsystem 1090 includes an interface 1092 to couple I/O subsystem 1090 with a high performance graphics engine 1038. In one embodiment, a bus may be used to couple graphics engine 1038 to I/O subsystem 1090. Alternately, a point-to-point interconnect 1039 may couple these components.

In turn, I/O subsystem 1090 may be coupled to a first bus 10110 via an interface 1096. In one embodiment, first bus 10110 may be a Peripheral Component Interconnect (PCI) bus, or a bus such as a PCI Express bus or another third generation I/O interconnect bus, although the scope of the present invention is not so limited.

As shown, various I/O devices 1014, 1024 may be coupled to first bus 10110, along with a bus bridge 1018 which may couple first bus 10110 to a second bus 1020. In one embodiment, second bus 1020 may be a low pin count (LPC) bus. Various devices may be coupled to second bus 1020 including, for example, a keyboard/mouse 1022, communication device(s) 1026 (which may in turn be in communication with a computer network), and a data storage unit 1028 such as a disk drive or other mass storage device which may include code 1030, in one embodiment. The code 1030 may include instructions for performing embodiments of one or more of the methods described above. Further, an audio I/O 1024 may be coupled to second bus 1020.

Note that other embodiments are contemplated. For example, instead of the point-to-point architecture shown, a system may implement a multi-drop bus or another such communication topology. Also, the elements of FIG. 6 may alternatively be partitioned using more or fewer integrated chips than shown in the FIG. 6.

Embodiments may forego certain components of FIG. 6 such as various bridges, graphics package 1038, keyboard/mouse 1022, and the like.

The following examples pertain to further embodiments.

Example 1 includes a functional near infrared (fNIR) system comprising: first, second, third, and fourth photo emitters; at least one photo detector; and at least one storage medium having instructions stored thereon for causing the system to: (a) emit first photo energy at first, second, third, and fourth wavelengths from the first, second, third, and fourth photo emitters during a first time period, (b) emit second photo energy at the first, second, third, and fourth wavelengths from the first, second, third, and fourth photo emitters during a second time period, (c) determine a first, second, third, and fourth optical density changes based on emitting the first and second photo energies; (e) determine a first change in a first chromophore concentration and a second change in a second chromophore concentration based on the determined first, second, third, and fourth optical density changes; (f) determine first, second, third, and fourth absorption values based on determining the first and second changes in the first and second chromophores; (g) fit the first, second, third, and fourth absorption values to first and second absorption spectra datasets corresponding to the first and second chromophores; and (h) determine at least one confidence level based on fitting the first, second, third, and fourth absorption values to first and second absorption spectra datasets.

In example 2 the subject matter of the Example 1 can optionally include wherein (a) the first, second, third, and fourth wavelengths are unequal to each other, and (b) the first and second wavelengths are between 650 nm and 800 nm and the third and fourth wavelengths are between 800 nm and 950 nm. Of course, other embodiments may address other ranges such as 700 nm-850 nm and 750 nm to 900 nm.

In example 3 the subject matter of Examples 1-2 can optionally include wherein the first and second absorption spectra datasets correspond to first and second absorption spectra curves.

In example 4 the subject matter of Examples 1-3 can optionally include wherein the first wavelength corresponds to a location at or less than an inflection point for the first absorption spectra curve and the second wavelength corresponds to an additional location greater than the inflection point.

In example 5 the subject matter of the Examples 1-4 can optionally include wherein the first chromophore is one of hemoglobin and oxygenated hemoglobin and the second chromophore is another of hemoglobin and oxygenated hemoglobin.

In example 6 the subject matter of the Examples 1-5 can optionally include wherein the first, second, third, and fourth photo emitters include light emitting diodes (LEDs).

In example 7 the subject matter of the Examples 1-6 can optionally include wherein the instructions cause the system to determine a first confidence level corresponding to fitting the first, second, third, and fourth absorption values to the first absorption spectra dataset and a second confidence level corresponding to fitting the first, second, third, and fourth absorption values to the second absorption spectra dataset.

For example, this may involve taking absorption values and fitting them to various curves searching for the best fits.

In example 8 the subject matter of the Examples 1-7 can optionally include wherein the instructions cause the system to determine a first confidence level corresponding to fitting the first and second absorption values to the first absorption spectra dataset and fitting the third and fourth absorption values to the second absorption spectra dataset.

For example, some embodiments take some values and fit them to a curve and fit other values to another curve. The same values may be compared to some of the same curves as well as other differing curves.

In example 9 the subject matter of the Examples 1-8 can optionally include wherein the instructions cause the system to determine a first confidence level corresponding to fitting the first, second, third, and fourth absorption values to the first and second absorption spectra datasets.

For example, some values are fit to multiple curves.

In example 10 the subject matter of the Examples 1-9 can optionally include wherein the first confidence level positively corresponds to when the first and second absorption values fit better to the first absorption spectra dataset than the second absorption spectra dataset and when the third and fourth absorption values fit better to the second absorption spectra dataset than the first absorption spectra dataset.

For example, such a case is shown in FIG. 5 where values are best fit to curve 510 in the wavelength range where hemoglobin is more readily recognized and values are best fit to curve 511 in the wavelength range where oxygenated hemoglobin is more readily recognized. In other words, this describes a more typical performance of oxygenated hemoglobin and hemoglobin thus leading to a higher confidence level.

In example 11 the subject matter of the Examples 1-10 can optionally include wherein the first confidence level negatively corresponds to when the first, second, third, and fourth absorption values fit better to the first absorption spectra dataset than the second absorption spectra dataset.

For example, such a case is shown in FIG. 3 where values are best fit to curve 310 in the wavelength range where hemoglobin is more readily recognized and where oxygenated hemoglobin is more readily recognized. In other words, this describes a less typical performance of oxygenated hemoglobin and hemoglobin thus leading to a lower confidence level.

In example 12 the subject matter of the Examples 1-11 can optionally include wherein the first, second, third, and fourth photo emitters are all generally equidistant from the at least one photo detector.

In example 13 the subject matter of the Examples 1-12 can optionally include fifth and sixth photo emitters; and wherein the instructions cause the system to (a) emit the first photo energy at fifth and sixth wavelengths from the fifth and sixth photo emitters during the first time period, (b) emit the second photo energy at the fifth and sixth wavelengths from the fifth and sixth photo emitters during the second time period, (c) determine fifth and sixth optical density changes based on emitting the first and second photo energies; (e) determine the first change in the first chromophore and the second change in the second chromophore based on the determined fifth and sixth optical density changes; (f) determine fifth and sixth absorption values based on determining the first and second changes in the first and second chromophores; (g) fitting the fifth and sixth absorption values to the first and second absorption spectra datasets; and (h) determine the at least one confidence level based on fitting the fifth and sixth absorption values to first and second absorption spectra datasets.

In example 14 the subject matter of the Examples 1-13 can optionally include wherein the instructions cause the system to determine a cognitive load based on the determined first and second changes in the first and second chromophores.

In example 15 the subject matter of the Examples 1-14 can optionally include wherein the instructions cause the system to determine, via an overdetermined system, the first and second changes in the first and second chromophore concentrations based on the determined first, second, third, and fourth optical density changes.

Example 16 includes a fNIR system comprising: first, second, and third light emitting diodes (LED) and a photo detector; and at least one storage medium having instructions stored thereon for causing the system to: (a) emit photo energy at first, second, and third wavelengths from the first, second, and third LEDs during first and second time periods, (b) determine first, second, and third optical density changes and changes in first and second chromophore concentrations based on the emitted photo energy; and (c) determine and fit first, second, and third absorption values to a first absorption spectra curve based on the determined changes in first and second chromophore concentrations.

Thus, not all embodiments necessarily require a confidence level be determined. In statistics, a confidence interval (CI) is a type of interval estimate of a population parameter. It is an observed interval (i.e. it is calculated from the observations), in principle different from sample to sample, that frequently includes the parameter of interest if the experiment is repeated. How frequently the observed interval contains the parameter is determined by the confidence level or confidence coefficient. More specifically, the meaning of the term "confidence level" is that, if confidence intervals are constructed across many separate data analyses of repeated (and possibly different) experiments, the proportion of such intervals that contain the true value of the parameter will match the confidence level.

In example 17 the subject matter of the Example 16 can optionally include wherein (a) the first, second, and third wavelengths are unequal to each other, and (b) the first and second wavelengths are between 650 nm and 800 nm and the third wavelength is between 800 nm and 950 nm.

In example 18 the subject matter of the Examples 16-17 can optionally include wherein the first wavelength corresponds to a location at or less than an inflection point for the first absorption spectra curve and the second wavelength corresponds to an additional location greater than the inflection point.

In example 19 the subject matter of the Examples 16-18 can optionally include wherein the instructions cause the system to determine a confidence level based on fitting the first, second, and third absorption values to the first absorption spectra curve.

In example 20 the subject matter of the Examples 16-19 can optionally include wherein the instructions cause the system to determine a confidence level based on fitting the first, second, and third absorption values to the first and second absorption spectra curves.

In example 21 the subject matter of the Examples 16-20 can optionally include wherein the confidence level positively corresponds to when the first and second absorption values fit better to the first absorption spectra curve than the second absorption spectra curve and when the third absorption values fits better to the second absorption spectra curve than the first absorption spectra curve.

Example 22 includes at least one storage medium having instructions stored thereon for causing a system to: (a) emit photo energy at first, second, and third wavelengths from first, second, and third LEDs during first and second time periods, (b) determine first, second, and third optical density changes and changes in first and second chromophore concentrations based on the emitted photo energy; and (c) determine and fit first, second, and third absorption values to at least one of first and second absorption spectra curves based on the determined changes in first and second chromophore concentrations.

Another embodiment of example 22 includes at least one storage medium having instructions stored thereon for causing a system to: determine first, second, and third optical density changes and changes in first and second chromophore concentrations based on photo energy emitted at first, second, and third wavelengths from first, second, and third LEDs during first and second time periods; and (b) determine and fit first, second, and third absorption values to at least one of first and second absorption spectra curves based on the determined changes in the first and second chromophore concentrations. Thus, an embodiment does not control lighting of LEDs but instead is more focused on analysis of resultant data and output of results (e.g., via display, auditory).

In example 23 the subject matter of the Example 22 can optionally include wherein (a) the first, second, and third wavelengths are unequal to each other, and (b) the first and second wavelengths are between 650 nm and 800 nm and the third wavelength is between 800 nm and 950 nm.

In example 24 the subject matter of the Examples 21-23 can optionally include wherein the first wavelength corresponds to a location at or less than an inflection point for the first absorption spectra curve and the second wavelength corresponds to an additional location greater than the inflection point.

In example 25 the subject matter of the Examples 21-24 can optionally include wherein the instructions cause the system to determine a confidence level based on fitting the first, second, and third absorption values to at least one of the first and second absorption spectra curves.

Example 1a includes a functional near infrared (fNIR) system comprising: first, second, third, and fourth photo emitters; at least one photo detector; and at least one storage medium having instructions stored thereon for causing the system to: (a) simultaneously emit photo energy at first, second, third, and fourth wavelengths from the first, second, third, and fourth photo emitters, (b) determine first, second, third, and fourth chromophore concentrations corresponding to the first, second, third, and fourth wavelengths, and (c) fitting a first plurality of the first, second, third, and fourth concentrations to a predetermined first absorption spectra dataset for a first chromophore to determine a first fit; wherein (d) the first, second, third, and fourth wavelengths are unequal to each other, (e) the first and second wavelengths are between 700 nm and 800 nm and the third and fourth wavelengths are between 800 nm and 900 nm.

In example 2a the subject matter of Example 1a can optionally include the system of claim 1, wherein the first, second, third, and fourth photo emitters include light emitting diodes (LEDs).

In example 3a the subject matter of Examples 1a-2a can optionally include wherein the instructions cause the system to determine a first confidence level corresponding to the determined first fit.

In example 4a the subject matter of Examples 1a-3a can optionally include wherein the instructions cause the system to fit at least one of the first plurality of the first, second, third, and fourth concentrations and a second plurality of the first, second, third, and fourth concentrations to a second predetermined absorption spectra dataset for a second chromophore to determine a second fit.

In example 5a the subject matter of Examples 1a-4a can optionally include wherein the instructions cause the system to determine a first confidence level corresponding to the determined second fit.

In example 6a the subject matter of Examples 1a-5a can optionally include wherein the instructions cause the system to determine a first confidence level corresponding to the determined first and second fits.

In example 7a the subject matter of Examples 1a-6a can optionally include wherein the first chromophore is one of hemoglobin and oxygenated hemoglobin and the second chromophore is another of hemoglobin and oxygenated hemoglobin.

In example 8a the subject matter of Examples 1a-7a can optionally include fifth and sixth photo emitters; and wherein the instructions cause the system to (a) simultaneously emit photo energy at the first, fifth, and sixth wavelengths from the first, fifth, and sixth photo emitters, (b) determine fifth and sixth concentrations corresponding to the fifth and sixth wavelengths, and (c) fit the fifth and sixth concentrations to the predetermined first absorption spectra dataset for a first chromophore to determine the first fit; wherein the first, second, fifth, and sixth wavelengths are unequal to each other and between 700 nm and 800 nm.

In example 9a the subject matter of Examples 1a-8a can optionally include wherein the first, second, third, and fourth photo emitters are all generally equidistant from the at least one photo detector.

Example 1b includes a method executed by at least one processor comprising: emitting first photo energy at first, second, third, and fourth wavelengths from first, second, third, and fourth photo emitters during a first time period; emitting second photo energy at the first, second, third, and fourth wavelengths from the first, second, third, and fourth photo emitters during a second time period; determining a first, second, third, and fourth optical density changes based on emitting the first and second photo energies; determining a first change in a first chromophore concentration and a second change in a second chromophore concentration based on the determined first, second, third, and fourth optical density changes; determining first, second, third, and fourth absorption values based on determining the first and second changes in the first and second chromophores; fitting the first, second, third, and fourth absorption values to first and second absorption spectra datasets corresponding to the first and second chromophores; and determining at least one confidence level based on fitting the first, second, third, and fourth absorption values to first and second absorption spectra datasets.

In example 2b the subject matter of the Example 1b can optionally include wherein (a) the first, second, third, and fourth wavelengths are unequal to each other, and (b) the first and second wavelengths are between 650 nm and 800 nm and the third and fourth wavelengths are between 800 nm and 950 nm. Of course, other embodiments may address other ranges such as 700 nm-850 nm and 750 nm to 900 nm.

In example 3b the subject matter of Examples 1-2b can optionally include wherein the first and second absorption spectra datasets correspond to first and second absorption spectra curves.

In example 4b the subject matter of Examples 1-3b can optionally include wherein the first wavelength corresponds to a location at or less than an inflection point for the first absorption spectra curve and the second wavelength corresponds to an additional location greater than the inflection point.

In example 5b the subject matter of the Examples 1-4b can optionally include wherein the first chromophore is one of hemoglobin and oxygenated hemoglobin and the second chromophore is another of hemoglobin and oxygenated hemoglobin.

In example 6b the subject matter of the Examples 1-5b can optionally include wherein the first, second, third, and fourth photo emitters include light emitting diodes (LEDs).

In example 7b the subject matter of the Examples 1-6b can optionally include wherein the instructions cause the system to determine a first confidence level corresponding to fitting the first, second, third, and fourth absorption values to the first absorption spectra dataset and a second confidence level corresponding to fitting the first, second, third, and fourth absorption values to the second absorption spectra dataset.

In example 8b the subject matter of the Examples 1-7b can optionally include determining a first confidence level corresponding to fitting the first and second absorption values to the first absorption spectra dataset and fitting the third and fourth absorption values to the second absorption spectra dataset.

In example 9b the subject matter of the Examples 1-8b can optionally include determining a first confidence level corresponding to fitting the first, second, third, and fourth absorption values to the first and second absorption spectra datasets.

In example 10b the subject matter of the Examples 1-9b can optionally include wherein the first confidence level positively corresponds to when the first and second absorption values fit better to the first absorption spectra dataset than the second absorption spectra dataset and when the third and fourth absorption values fit better to the second absorption spectra dataset than the first absorption spectra dataset.

In example 11b the subject matter of the Examples 1-10b can optionally include wherein the first confidence level negatively corresponds to when the first, second, third, and fourth absorption values fit better to the first absorption spectra dataset than the second absorption spectra dataset.

In example 12b the subject matter of the Examples 1-11b can optionally include wherein the first, second, third, and fourth photo emitters are all generally equidistant from the at least one photo detector.

In example 13b the subject matter of the Examples 1-12b can optionally include emitting the first photo energy at fifth and sixth wavelengths from fifth and sixth photo emitters during the first time period; emitting the second photo energy at the fifth and sixth wavelengths from the fifth and sixth photo emitters during the second time period; determining fifth and sixth optical density changes based on emitting the first and second photo energies; determining the first change in the first chromophore and the second change in the second chromophore based on the determined fifth and sixth optical density changes; determining fifth and sixth absorption values based on determining the first and second changes in the first and second chromophores; (g) fitting the fifth and sixth absorption values to the first and second absorption spectra datasets; and determining the at least one confidence level based on fitting the fifth and sixth absorption values to the first and second absorption spectra datasets.

In example 14b the subject matter of the Examples 1-13b can optionally include determining a cognitive load based on the determined first and second changes in the first and second chromophores.

In example 15b the subject matter of the Examples 1-14b can optionally include determining, via an overdetermined system, the first and second changes in the first and second chromophore concentrations based on the determined first, second, third, and fourth optical density changes.

Example 16b includes a method executed by at least one processor comprising: emitting photo energy at first, second, and third wavelengths from first, second, and third LEDs during first and second time periods; determining first, second, and third optical density changes and changes in first and second chromophore concentrations based on the emitted photo energy; and determining and fitting first, second, and third absorption values to a first absorption spectra curve based on the determined changes in the first and second chromophore concentrations.

In example 17b the subject matter of the Example 16b can optionally include wherein (a) the first, second, and third wavelengths are unequal to each other, and (b) the first and second wavelengths are between 650 nm and 800 nm and the third wavelength is between 800 nm and 950 nm.

In example 18b the subject matter of the Examples 16-17b can optionally include wherein the first wavelength corresponds to a location at or less than an inflection point for the first absorption spectra curve and the second wavelength corresponds to an additional location greater than the inflection point.

In example 19b the subject matter of the Examples 16-18b can optionally include determining a confidence level based on fitting the first, second, and third absorption values to the first absorption spectra curve.

In example 20b the subject matter of the Examples 16-19b can optionally include determining a confidence level based on fitting the first, second, and third absorption values to the first and second absorption spectra curves.

Example 21b includes a method executed by at least one processor comprising: emitting photo energy at first, second, and third wavelengths from first, second, and third LEDs during first and second time periods; determining first, second, and third optical density changes and changes in first and second chromophore concentrations based on the emitted photo energy; and determining and fit first, second, and third absorption values to at least one of first and second absorption spectra curves based on the determined changes in the first and second chromophore concentrations.

Another embodiment of example 21b includes a method executed by at least one processor comprising: determining first, second, and third optical density changes and changes in first and second chromophore concentrations based on photo energy emitted at first, second, and third wavelengths from first, second, and third LEDs during first and second time periods; and determining and fit first, second, and third absorption values to at least one of first and second absorption spectra curves based on the determined changes in the first and second chromophore concentrations.

In example 22b the subject matter of the Example 21b can optionally include wherein (a) the first, second, and third wavelengths are unequal to each other, and (b) the first and second wavelengths are between 650 nm and 800 nm and the third wavelength is between 800 nm and 950 nm.

In example 23b the subject matter of the Examples 21-22b can optionally include wherein the first wavelength corresponds to a location at or less than an inflection point for the first absorption spectra curve and the second wavelength corresponds to an additional location greater than the inflection point.

In example 24b the subject matter of the Examples 21-23b can optionally include determining a confidence level based on fitting the first, second, and third absorption values to at least one of the first and second absorption spectra curves.

In example 25b the subject matter of the Examples 21-24b can optionally include at least one machine readable medium comprising a plurality of instructions that in response to being executed on a computing device, cause the computing device to carry out a method according to any one of examples 1b to 24b.

Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. A functional near infrared (fNIR) system comprising:
first, second, third, and fourth photo emitters;
at least one photo detector; and
at least one non-transitory storage medium having executable instructions stored thereon that, when executed, cause a processor of the system to: (a) emit first photo energy at first, second, third, and fourth wavelengths from the first, second, third, and fourth photo emitters during a first time period, (b) emit second photo energy at the first, second, third, and fourth wavelengths from the first, second, third, and fourth photo emitters during a second time period, (c) determine first, second, third, and fourth optical density changes based on emitting the first and second photo energies; (d) determine a first change in a first chromophore concentration and a second change in a second chromophore concentration based on the determined first, second, third, and fourth optical density changes; (e) determine first, second, third, and fourth absorption values based on determining the first and second changes in the first and second chromophores; (f) fit the first, second, third, and fourth absorption values to first and second absorption spectra datasets corresponding to the first and second chromophores; and (g) determine at least one confidence level based on fitting the first, second, third, and fourth absorption values to first and second absorption spectra datasets.

2. The system of claim 1, wherein (a) the first, second, third, and fourth wavelengths are unequal to each other, and (b) the first and second wavelengths are between 650 nm and 800 nm and the third and fourth wavelengths are between 800 nm and 950 nm.

3. The system of claim 2, wherein the first and second absorption spectra datasets correspond to first and second absorption spectra curves.

4. The system of claim 3, wherein the first wavelength corresponds to a location at or less than an inflection point for the first absorption spectra curve and the second wavelength corresponds to an additional location greater than the inflection point.

5. The system of claim 4, wherein:
the first chromophore is one of hemoglobin and oxygenated hemoglobin and the second chromophore is another of hemoglobin and oxygenated hemoglobin; and
at least one of the first, second, third, and fourth wavelengths is greater than 900 nm.

6. The system of claim 1, wherein the first, second, third, and fourth photo emitters include light emitting diodes (LEDs).

7. The system of claim 1, wherein the instructions cause the system to determine a first confidence level corresponding to fitting the first, second, third, and fourth absorption values to the first absorption spectra dataset and a second confidence level corresponding to fitting the first, second, third, and fourth absorption values to the second absorption spectra dataset.

8. The system of claim 1, wherein the instructions cause the system to determine a first confidence level corresponding to fitting the first and second absorption values to the first absorption spectra dataset and fitting the third and fourth absorption values to the second absorption spectra dataset.

9. The system of claim 1, wherein the instructions cause the system to determine a first confidence level corresponding to fitting the first, second, third, and fourth absorption values to the first and second absorption spectra datasets.

10. The system of claim 9, wherein the first confidence level positively corresponds to when the first and second absorption values fit better to the first absorption spectra dataset than the second absorption spectra dataset and when the third and fourth absorption values fit better to the second absorption spectra dataset than the first absorption spectra dataset.

11. The system of claim 10, wherein the first confidence level negatively corresponds to when the first, second, third, and fourth absorption values fit better to the first absorption spectra dataset than the second absorption spectra dataset.

12. The system of claim 1, wherein the first, second, third, and fourth photo emitters are all generally equidistant from the at least one photo detector.

13. The system of claim 1 comprising:
fifth and sixth photo emitters;
wherein the instructions cause the system to (a) emit the first photo energy at fifth and sixth wavelengths from the fifth and sixth photo emitters during the first time period, (b) emit the second photo energy at the fifth and sixth wavelengths from the fifth and sixth photo emitters during the second time period, (c) determine fifth and sixth optical density changes based on emitting the first and second photo energies; (d) determine the first change in the first chromophore and the second change in the second chromophore based on the determined fifth and sixth optical density changes; (e) determine fifth and sixth absorption values based on determining the first and second changes in the first and second chromophores; (f) fitting the fifth and sixth absorption values to the first and second absorption spectra datasets; and (g) determine the at least one confidence level based on fitting the fifth and sixth absorption values to the first and second absorption spectra datasets.

14. The system of claim 1, wherein the instructions cause the system to determine a cognitive load based on the determined first and second changes in the first and second chromophores.

15. The system of claim 1, wherein the instructions cause the system to determine, via an overdetermined system, the first and second changes in the first and second chromophore concentrations based on the determined first, second, third, and fourth optical density changes.

16. A functional near infrared (fNIR) system comprising:
first, second, and third light emitting diodes (LED) and a photo detector; and
at least one non-transitory storage medium having executable instructions stored thereon that, when executed, cause a processor of the system to: (a) emit photo energy at first, second, and third wavelengths from the first, second, and third LEDs during first and second time periods, (b) determine first, second, and third optical density changes and changes in first and second chromophore concentrations based on the emitted photo energy; and (c) determine and fit first, second, and third absorption values to a first absorption spectra curve in response to determining changes in the first and second chromophore concentrations.

17. The system of claim 16, wherein (a) the first, second, and third wavelengths are unequal to each other, and (b) the first and second wavelengths are between 650 nm and 800 nm and the third wavelength is between 800 nm and 950 nm.

18. The system of claim 17, wherein the first wavelength corresponds to a location at or less than an inflection point for the first absorption spectra curve and the second wavelength corresponds to an additional location greater than the inflection point.

19. The system of claim 16, wherein the instructions cause the system to determine a confidence level based on fitting the first, second, and third absorption values to the first absorption spectra curve.

20. The system of claim 16, wherein the instructions cause the system to determine a confidence level based on fitting the first, second, and third absorption values to the first and second absorption spectra curves.

21. The system of claim 20, wherein the confidence level positively corresponds to when the first and second absorption values fit better to the first absorption spectra curve than the second absorption spectra curve and when the third absorption values fits better to the second absorption spectra curve than the first absorption spectra curve.

22. At least one non-transitory storage medium having executable instructions stored thereon that, when executed, cause a processor of the system to:
(a) emit photo energy at first, second, and third wavelengths from first, second, and third LEDs during first and second time periods, (b) determine first, second, and third optical density changes and changes in first and second chromophore concentrations based on the emitted photo energy; (c) determine and fit first, second, and third absorption values to at least one of first and second absorption spectra curves; and (d) determine a confidence level based on fitting the first, second, and third absorption values to at least one of the first and second absorption spectra curves.

23. The at least one medium of claim 22, wherein (a) the first, second, and third wavelengths are unequal to each other, and (b) the first and second wavelengths are between 650 nm and 800 nm and the third wavelength is between 800 nm and 950 nm.

24. The at least one medium of claim 23, wherein the first wavelength corresponds to a location at or less than an inflection point for the first absorption spectra curve and the second wavelength corresponds to an additional location greater than the inflection point.

* * * * *